(12) United States Patent
Santti et al.

(10) Patent No.: US 7,825,107 B2
(45) Date of Patent: Nov. 2, 2010

(54) METHOD OF TREATING MEN SUFFERING FROM CHRONIC NONBACTERIAL PROSTATITIS WITH SERM COMPOUNDS OR AROMATASE INHIBITORS

(75) Inventors: Risto Santti, Turku (FI); Tomi Streng, Turku (FI); Jenni Bernoulli, Turku (FI); Emrah Yatkin, Turku (FI)

(73) Assignee: Hormos Medical Ltd., Turku (FI)

( * ) Notice: Subject to any disclaimer, the term of this patent is extended or adjusted under 35 U.S.C. 154(b) by 503 days.

(21) Appl. No.: 11/751,846

(22) Filed: May 22, 2007

(65) Prior Publication Data

US 2008/0021111 A1 Jan. 24, 2008

Related U.S. Application Data

(60) Provisional application No. 60/802,657, filed on May 22, 2006.

(51) Int. Cl.
*A61K 31/56* (2006.01)
*A61K 31/19* (2006.01)
*A61K 31/16* (2006.01)

(52) U.S. Cl. .................. 514/171; 514/570; 514/613

(58) Field of Classification Search ................. 514/171, 514/570, 613
See application file for complete search history.

(56) References Cited

U.S. PATENT DOCUMENTS

| | | | |
|---|---|---|---|
| 4,536,516 A | 8/1985 | Harper et al. | |
| 4,656,187 A | 4/1987 | Black et al. | |
| 4,696,949 A | 9/1987 | Toivola et al. | |
| 4,839,155 A | 6/1989 | McCague | |
| 4,894,373 A | 1/1990 | Young | |
| 4,977,906 A | 12/1990 | Di Scipio | |
| 4,996,225 A | 2/1991 | Toivola et al. | |
| 5,118,667 A | 6/1992 | Adams et al. | |
| 5,189,212 A | 2/1993 | Ruenitz | |
| 5,192,525 A | 3/1993 | Yang et al. | |
| 5,196,435 A | 3/1993 | Clemens et al. | |
| 5,446,203 A | 8/1995 | McNelis | |
| 5,470,883 A | 11/1995 | Stromberg | |
| 5,491,173 A | 2/1996 | Toivola et al. | |
| 5,658,931 A | 8/1997 | Bryant et al. | |
| 5,691,355 A | 11/1997 | Bryant et al. | |
| 5,693,674 A | 12/1997 | Bitonti | |
| 5,703,109 A | 12/1997 | Karjalainen et al. | |
| 5,719,136 A | 2/1998 | Chwalisz et al. | |
| 5,750,576 A | 5/1998 | DeGregorio et al. | |
| 5,807,899 A | 9/1998 | Bohlmann et al. | |
| 5,821,254 A | 10/1998 | Sporn et al. | |
| 5,827,892 A | 10/1998 | Löser et al. | |
| 5,852,059 A | 12/1998 | Thompson | |
| 5,861,389 A | 1/1999 | Radlmaier et al. | |
| 5,877,219 A | 3/1999 | Willson | |
| 5,912,273 A | 6/1999 | Degregorio et al. | |
| 5,972,921 A | 10/1999 | Santi et al. | |
| 6,037,379 A | 3/2000 | Härkönen et al. | |
| 6,316,431 B1 | 11/2001 | Santti et al. | |
| 6,576,645 B1 | 6/2003 | Södervall et al. | |
| 6,608,111 B1 * | 8/2003 | Meyers et al. ............... 514/570 |
| 6,686,351 B2 | 2/2004 | Bhagwat | |
| 6,875,775 B2 | 4/2005 | Södervall et al. | |

FOREIGN PATENT DOCUMENTS

| | | |
|---|---|---|
| EP | 0 095 875 A2 | 12/1983 |
| EP | 0 779 808 B1 | 8/1999 |
| EP | 1 199 069 A2 | 4/2002 |
| GB | 1064629 | 4/1967 |
| WO | WO 92/06068 | 4/1992 |
| WO | WO 93/19746 | 10/1993 |
| WO | WO 94/13645 | 6/1994 |
| WO | WO 95/26720 | 10/1995 |
| WO | WO 96/07402 | 3/1996 |
| WO | WO 9609057 | 3/1996 |
| WO | WO 96/35417 | 11/1996 |
| WO | WO 96/40616 | 12/1996 |
| WO | WO 97/26876 | 7/1997 |
| WO | WO 97/32574 | 9/1997 |
| WO | WO 98/11888 A1 | 3/1998 |
| WO | WO 99/42427 | 8/1999 |
| WO | WO 99/42427 A1 | 8/1999 |
| WO | WO 99/63974 | 12/1999 |
| WO | WO 00/55137 | 9/2000 |
| WO | WO 01/36360 A1 | 5/2001 |
| WO | WO 02/03989 A2 | 1/2002 |
| WO | WO 03/039524 A1 | 5/2003 |

OTHER PUBLICATIONS

Harkonen et al., The Journal of Steroid Biochemistry & Molecular Biology, 2004;92:297-305.*

(Continued)

*Primary Examiner*—San-ming Hui
(74) *Attorney, Agent, or Firm*—Brinks Hofer Gilson & Lione

(57) ABSTRACT

A method for treatment or prevention of chronic nonbacterial prostatitis in individuals without urethral sphincter dysfunction, comprises administering an effective amount of (i) a selective estrogen receptor modulator (SERM) having estrogen antagonist effect in the prostate, (ii) an aromatase inhibitor, and/or (iii) an antiestrogen.

2 Claims, No Drawings

OTHER PUBLICATIONS

Bentrem, D.J., et al., "Tamoxifen, raloxifene and the prevention of breast cancer", Minerva Endocrinologica, vol. 27, No. 2, 2002, pp. 127-139.

Budavari, S. et al., eds., *The Merck Index, Eleventh Edition*, p. 1430, No. 9019, Merck & Co., Inc., Rathway, NJ, USA (1989).

Budavari, S. et al., eds., *The Merck Index, Eleventh Edition*, p. 1433, No. 9039, Merck & Co., Inc., Rathway, NJ, USA (1989).

de Lignieres, B., "Transdermal Dihydrotestosterone Treatment of Andropause," 25 *Ann Med* 235-241 (1993).

Doran, P.M., "Effects of Raloxifene, a Selective Estrogen Receptor Modulator, on Bone Turnover Markers and Serum Sex Steroid and Lipid Levels in Elderly Men", Journal of Bone and Mineral Research, vol. 16, No. 11, 2001, pp. 2118-2125.

Gingell, J.G., et al., "Placebo Controlled Double-Blind Study to Test the Efficacy of the Aromatase Inhibitor Atamestane in Patients with Benign Prostatic Hyperplasia not Requiring Operation," *J. Urol.* 154:399-401 (Aug. 1995).

Glass, A.R., MD "Gynecomastia," 23 *Clinical Andrology* 825-837 (Dec. 1994).

Goldstein, S.R. et al., "A pharmacological review of selective oestrogen receptor modulators," *Human Reproduction Update* 6:212-224, Oxford University Press (May-Jun. 2000).

Grodstein, F. and Stampfer, M.J., "Estrogen for women at varying risk of coronary disease," *Maturitas* 30:19-26, Elsevier Science Ireland Ltd. (1998).

Hakenberg, O.W., et al., "Chronic Pelvic Pain in Men," *Urol. Intl.* 68:138-143 (2002).

Henderson, V.W., "Estrogen, Cognition, and a Woman's Risk of Alzheimer's Disease," *The American Journal of Medicine* 103:115-18S, Excerpta Medica, Inc. (1997).

International Search Report for corresponding International Application No. PCT/FI00/00946, mailed Feb. 8, 2001.

Jordan, V.C., "Antiestrogens and Selective Estrogen Receptor Modulators as Multifunctional Medicines. 2. Clinical Considerations and New Agents," *J. Med. Chem.* 46(7):1081-1111 (Mar. 2003).

Kangas, L. et al., "A new triphenylethylene compound, Fc-1157a: II. Anti effects," *Cancer Chemother. Pharmacol.* 17:109-113, Springer-Verlag (1986).

Kangas, L. et al., "Bioluminescence of Cellular ATP: A New Method for Evaluating Cytotoxic Agents In Vitro," *Medical Biology* 62:338-343, Duodecim (1984).

Kangas, L., "Biochemical and Pharmacological Effects of Toremifene Metabolites," *Cancer Chemo. Pharmacol.* 27:8-12 (Apr. 1990).

Karjalainen, A. et al. (2000). "Synthesis of new potent and selective aromatase inhibitors based on long-chained diarylalkylimidazole and diarylalkyltriazole molecule skeletons," *Eur. J. Pharm. Sci.* 11:109-131.

Khovidhunkit, W. and Shoback, D.M., "Clinical Effects of Raloxifene Hydrochloride in Women," *Ann. Intern. Med.* 130:431-439, American College of Physicians (Mar. 1999).

Licata, A.A., et al., "Raloxifene: A new choice for treating and preventing osteoporosis", Osteoporosis Update reprinted from Cleveland Clinic Journal of Medicine, vol. 67, No. 4, Apr. 2000, pp. 273-280, reprinted as pp. 19-26.

Lobo, R.A., "Benefits and risks and estrogen replacement therapy," *Am. J. Obstet. Gynecol.* 173:982-989, Mosby-Year Book, Inc. (1995).

Macgregor, J.I. and Jordan, V.C., "Basic Guide to the Mechanisms of Antiestrogen Action," *Pharmacol. Rev.* 50:151-196, Williams and Wilkins Co. (1998).

Oesterling, J.E. et al. (1988) "Aromatase Inhibition in the DOG. II. Effect on Growth, Function, and Pathology of the Prostate", The Journal of Urology, vol. 139 Apr.:832-839.

Peng, Z. et al., "The Mechanical Strength of Bone in Different Rat Models of Experimental Osteoporosis," *Bone* 15:523-532, Elsevier Science Ltd. (1994).

Plouffe, L., "Selective Estrogen Receptor Modulators (SERMs) in Clinical Practice," *J. Soc. Gynecol. Investig.* 7:S38-S46, Elsevier Science Inc. (Jan.-Feb. 2000).

Qu, Q. et al., "Selective Estrogenic Effects of a Novel Triphenylethylene Compound, FC1271a, on Bone, Cholesterol Level, and Reproductive Tissues in Intact and Ovariectomized Rats," *Endocrinology* 14:809-820, Association for the Study of Internal Secretions (Fed. 2000).

Radlmaier A. et al., "Estrogen Reduction by Aromatase Inhibition for Benign Prostatic Hyperplasia: Results of a Double-Blind, Placebo-Controlled, Randomized Clinical Trial Using Two Doses of the Aromatase-Inhibitor Atamestane," *The Prostate* 29:199-208 (1996).

Renaud, J., et al., "Estrogen Receptor Modulators: Identification and Structure—Activity Relationships of Potent Erα-Selective Tetrahydroisoquinoline Ligands", J. Med. Chem., vol. 46, 2003, pp. 2945-2957.

Robinson, D., et al., "Overactive Bladder in the Female Patient: The Role of Estrogens", Current Urology Reports, vol. 3, 2002, pp. 452-457.

Robinson, D., et al., "The Role of Estrogens in Female Lower Urinary Tract Dysfunction", Urology, vol. 62, Supp. 4A, Oct. 2003, pp. 45-50.

Santti et al.; Final Office Action from U.S. Appl. No. 10/454,823, filed Jun. 5, 2003.

Schilcher, H., "Miktionsbeeinflussende Mittel zur Behandlung der BPH," *Phytotherapie in der Urologie* 69-93 (1992).

Shuk-Mei Ho, "Estrogens and Anti-Estrogens: Key Mediators and Prostate Carcinogenesis and New Therapeutic Candidates", Journal of Cellular Biochemistry, vol. 91, 2004, pp. 491-503.

Simberg, N.H. et al., "In Vitro and In Vitro Binding of Toremifene and Its Metabolites in Rat Uterus," *J. Steroid Biochem.* 36:197-202, Pergamon Press: plc (1990).

Smetnik V.P. "Postmenopausal Disorders and Methods for Correcting Thereof"; Consilium-Medicum, 2001, No. 11, vol. 3; (Translation —pp. 1-3).

Smetnik V.P. "Postmenopausal Disorders and Methods for Correcting Thereof"; Consilium-Medicum, 2001, No. 11, vol. 3; pp. 1-4; 14.

Steiner, M.S., et al., "Selection Estrogen Receptor Modulators for the Chemoprevention of Prostate Cancer", Urology, vol. 57, Supp. 4A, Apr. 2001, pp. 68-72.

Terenius, L., "Structure-Activity Relationships of Anti-Ostrogens With Regard to Interaction With 17β-Oestradiol in the Mouse Uterus and Vargina," *Acta Endocrinol.* 66:431-447, Scandinavian University Press (1971).

Usman Azam et al., "Economics of Lower Urinary Tract Symptoms (LUTS) in Older People", Drugs and Aging, vol. 18(3), 2001, pp. 214-223.

Yue, et al.; "Selective Estrogen Receptor Modulator Idoxifene Inhibits Smooth Muscle Cell Proliferation, Enhances Reendothelialization, and Inhibits Neointimal Formation In Vivo After Vascular Injury"; Departments of Cardiovascular Pharmacology and Experimental Toxicology; pp. III-281-III-288; Nov. 7, 2000.

\* cited by examiner

METHOD OF TREATING MEN SUFFERING FROM CHRONIC NONBACTERIAL PROSTATITIS WITH SERM COMPOUNDS OR AROMATASE INHIBITORS

This application claims the benefit of U.S. Provisional Application No. 60/802,657, filed May 22, 2006, which is incorporated by reference.

BACKGROUND OF THE INVENTION

1. Field of the Invention

The invention is directed to a method of treating men suffering from chronic nonbacterial prostatitis with a selective estrogen receptor modulator (SERM) compound, an aromatase inhibitor and/or an antiestrogen.

2. Description of Related Art

Prostatitis is an inflammatory disorder of the prostate, which close to 50 percent of all men suffer at some stage of their life. Chronic nonbacterial prostatitis involves inflammation of the prostate gland and commonly affects men of all ages. It can cause chronic pelvic pain syndrome (CPPS), problems urinating, including discomfort and pain, increased frequency and urge, or problems emptying the bladder.

In a suitable hormonal milieu, with androgens present, chronic nonbacterial prostatitis may progress to prostate overgrowth (benign prostatic hyperplasia ("BPH")), and to prostate cancer.

Selective estrogen receptor modulators ("SERMs") are compounds binding to estrogen receptors in different tissues but exercising either antagonistic or agonistic effects. Compounds like tamoxifen, toremifene, raloxifene, lasofoxifene, bazedoxifene, ospemifene and fispemifene are typical SERMs. They share some common characteristics such as being antiestrogenic in breast cancer and estrogenic in bone, whereas in other organs they show varying degrees of estrogenic or antiestrogenic properties. In the urinary tract, the antiestrogenic properties seem to prevail.

Experimental models have shown that selective estrogen receptor modulators (SERMs) may be useful for treating or preventing lower urinary tract symptoms (LUTS). A method for the treatment or prevention of lower urinary tract symptoms, including nonbacterial prostatitis, with SERMs is fully disclosed in U.S. patent application Ser. No. 10/454,823, incorporated herein by reference.

U.S. Pat. No. 5,972,921, incorporated herein by reference, teaches treatment of urethral sphincter dysfunction, which causes LUTS by aromatase inhibitors.

The basis for treating urinary tract symptoms with SERMs or aromatase inhibitors is the observation that an increase of the ratio of estradiol to testosterone results in the development of urethral sphincter dysfunction, which causes LUTS. However, although chronic nonbacterial prostatitis with pelvic pain may sometimes be associated with urethral sphincter dysfunction, the cause of chronic nonbacterial prostatitis has not previously been shown to be estrogen dependent.

In men, obstruction of the urethra by benign prostatic hyperplasia (BPH), a benign enlargement of the prostate, is frequently considered to be the major cause of LUTS. However, several studies have shown that there is only a weak correlation between prostate enlargement, obstruction and LUTS.

SUMMARY OF THE INVENTION

It has now been found that chronic nonbacterial prostatitis is estrogen dependent. Increased estrogen to androgen concentration ratio in adult Noble rats causes nonbacterial prostatitis as a direct effect in the prostate without simultaneous urethral sphincter dysfunction. Prostatitis in rats is determined by observation of inflammatory cells, and the histology has been found to be similar to that in men.

Consequently, the present invention is a method of treating chronic nonbacterial prostatitis in men, wherein the chronic nonbacterial prostatitis is not associated with urethral sphincter dysfunction. The method comprises administering an effective amount of (i) a selective estrogen receptor modulator having antiestrogenic effect in the prostate, (ii) an aromatase inhibitor, and/or (iii) an anti-estrogen, to a patient in need thereof.

The invention is also a method of preventing the progression of BPH and, prostate cancer. Development of stromal overgrowth (homologous to stromal overgrowth in human BPH) and development of prostate cancer are associated with long term duration of chronic prostatitis. Treating the chronic prostatitis with SERMs, e.g. fispemifene, or aromatase inhibitors or antiestrogen, will prevent progression of BPH or development of prostate cancer.

DETAILED DESCRIPTION OF THE INVENTION

The inventors have found that SERMs, such as fispemifene, antagonize the estrogen effect in the prostate and may thus be used to prevent or treat chronic nonbacterial prostatitis. Similarly, lowering of estrogen concentration in the body by using aromatase inhibitors, or by using anti-estrogens, can be used to treat this condition.

To show the influence of increased estrogen to testosterone ratio on chronic nonbacterial prostatitis, a first group of Noble rats were treated for 6 weeks with testosterone (T) (240 ug/day) and estradiol (E2) (70 ug/day), to produce a profile in the animals of normal T/high E2. (Ratio of T/E2 was 30 in the test group compared to 150 in controls; T concentration was 0.8 ng/ml compared to 1.5 in control; E2 concentration 30 pg/ml compared to 10 pg/ml in controls.) The animals exhibited nonbacterial prostatitis in the absence of obstructed voiding, and normal size prostate.

To show the effects of a higher ratio of estradiol, in a low testosterone milieu, Noble rats were treated for 13 weeks with T (240 ug/d) and E2 (70 ug/d), exhibiting a profile of low T/high E2. (Ratio of T/E2 was 1 to 10 in the test group, compared to 150 in controls; testosterone concentration was 100 pg/ml compared to 1.5 ng/ml in control; estradiol concentration was 40-80 pg/ml compared to 10 pg/ml in the controls.) The animals in this group exhibited chronic nonbacterial prostatitis, without significant urodynamic changes, and again in the absence of obstructed voiding. The animals exhibited small prostate, but with stromal overgrowth similar to benign prostatic hyperplasia in men.

To demonstrate the effects of an elevated estradiol-to-testosterone ratio in the context of a high testosterone milieu, a third group of Noble rats was treated for 13 weeks with T (800 ug/d) and E2 (70 ug/d). The ratio of T/E2 was 75 in the test group compared to 150 in controls. Testosterone concentration was 4.5 ng/ml in the test group compared to 1.5 ng/ml in controls. The estradiol concentration was 60 pg/ml compared to 10 pg/ml in the controls). The prostate in these animals was larger than normal, exhibiting chronic prostatitis and precancerous lesions and ductal carcinomas of the prostate, suggestive of a trend toward development of BPH and prostate cancer.

To demonstrate the use of an estrogen antagonist to treat chronic nonbacterial prostatitis, a fourth group of rats was treated for 3 weeks with T (240 ug/day) and E2 (70 ug/day), and thereafter administered 2 doses of a pure estrogen antagonist fulvestrant (5 mg/kg) on the third week. Fulvestrant significantly reduced the prostatitis compared to the control group treated with T and E2 only. As prostatitis can be reversed by administering an antiestrogen, the condition is seen to be estrogen dependent.

To demonstrate the estrogen antagonist effect of fispemifene in the prostate, a fifth group of Noble rats was castrated and treated for three weeks with fispemifene at doses of 3, 10 and 30 mg/kg, with and without concomitant estradiol administration (70 ug/day ). It was observed that fispemifene was an estrogen antagonist in the prostate, and dose dependently inhibited the effect of estradiol on the prostate, measured by FRA2 or PR expression, which are sensitive markers of estrogen effect.

It is believed that doses of 0.1 to 100 mg/kg of fispemifene (or other SERM) administered to human males by various routes including, without limitation, oral, topical, transdermal, or subcutaneous routes, will have an estrogen antagonist effect in the prostate to treat chronic nonbacterial prostatitis and/or prevent the development of BPH and prostate cancer. A preferred dosage range is about 0.1 to about 10.0 mg/kg, with expected daily dosages expected to be in the range of about 100 mg to about 300 mg per person. It is believed the oral administration route is the most preferable. Suitable preparation forms include for example tablets, capsules, granules, powders, suspensions, and syrups.

What is claimed is:

1. A method of treating chronic nonbacterial prostatitis in men, comprising administering to a patient in need thereof an effective amount of fispemifene wherein said chronic nonbacterial prostatitis is not associated with urethral sphincter dysfunction.

2. The method of claim 1, comprising the step of administering fispemifene in an amount in a range of about 0.1 to about 100 mg/kg of body weight.

* * * * *

UNITED STATES PATENT AND TRADEMARK OFFICE
Certificate

Patent No. 7,825,107 B2					Patented: November 2, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Risto Santti, Turku (FI); Tomi Streng, Turku (FI); Kaija Halonen, Rusko (FI); Jenni Bernoulli, Turku (FI); and Emrah Yatkin, Turku (FI).

Signed and Sealed this Twenty-fourth Day of September 2013.

MELENIE MCCORMICK
*Supervisory Patent Examiner*
Art Unit 1629
Technology Center 1600